United States Patent [19]

Umezawa et al.

[11] 4,151,347

[45] Apr. 24, 1979

[54] SEPARATION OF COFORMYCIN AND ITS RELATED NUCLEOSIDES

[75] Inventors: Hamao Umezawa, Tokyo; Shinichi Kondo, Yokohama, both of Japan

[73] Assignee: Zaidan Hojin Biseibutsu Kagaku Kenkyu Kai, Tokyo, Japan

[21] Appl. No.: 881,258

[22] Filed: Feb. 27, 1978

[30] Foreign Application Priority Data

Mar. 15, 1977 [JP]  Japan ................................. 52-27648

[51] Int. Cl.$^2$ ...................... C07H 17/00; A61K 31/70
[52] U.S. Cl. ..................................... 536/24; 424/180; 536/26
[58] Field of Search ......................................... 536/24

[56] References Cited

U.S. PATENT DOCUMENTS 3,923,785  12/1975  Ryder et al. ............................ 536/24
3,959,257  5/1976  Umegawa et al. ...................... 536/24

*Primary Examiner*—Johnnie R. Brown
*Assistant Examiner*—Blondel Hazel
*Attorney, Agent, or Firm*—Haight & Huard

[57] ABSTRACT

A known nucleoside, coformycin and its related substances such as isocoformycin, 2'-deoxycoformycin and formycins present as a mixture of them may be separated from each other when an aqueous solution containing them is chromatographed on a column of a cation-exchanger having partially activated carboxylic groups as the ion-exchange function with using water or a buffer solution as the developing solvent.

9 Claims, No Drawings

SEPARATION OF COFORMYCIN AND ITS RELATED NUCLEOSIDES

SUMMARY OF THE INVENTION

This invention relates to a process for separating coformycin and its related nucleosides present as a mixture of at least two of coformycin and said related nucleosides, either to isolate coformycin from the other nucleosides or to isolate them from each other. More particularly, this invention relates to a process of for separating coformycin and its related nucleosides such as isocoformycin, 2'-deoxycoformycin and formycins present as a mixture of at least two of them, by subjecting an aqueous solution of said mixture to chromatography on a column of a weak cation-exchanger having carboxylic ion-exchange groups which have been partially activated, collecting the eluate in fractions, and then recovering coformycin and its related nucleosides independently from each other or recovering coformycin separately from its related nucleosides out of the separate fractions of the eluate.

BACKGROUND OF THE INVENTION

Coformycin is a known unusual nucleoside discovered by H. Umezawa et al. and obtained from the culture broth of *Nocardia interforma* (ATCC No. 21072) and *Streptomyces kaniharaensis* SF-557 (ATCC No. 21070) which are the microorganisms producing the nucleoside antibiotics formycins A and B (see Japanese patent publication No. 12278/70 and the "Journal of Antibiotics" Ser. A. 17:, 96 (1964)). Coformycin may also be obtained from the culture broth of *Streptomyces lavendulae* MA25-A2. Coformycin has interesting biological and physiological properties such as an activity to inhibit remarkably the enzymatic deamination of formycin A and adenosine by adenosine deaminase (see the "Journal of Antibiotics" Ser. A, 20: 227, (1967)). Accordingly, coformycin is a very useful substance not only for the analysis of causes of diseases involving the metabolism of nucleic acid, but also for the chemotherapy of certain diseases, including tumors. Coformycin has the following chemical structure:

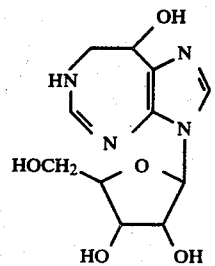

(see the "Journal of the American Chemical Society" 96: 4327 (1974)) and may be synthesized chemically from 9-β-D-ribofuranosylpurine (see Japanese Pat. No. 875,639 and the "Journal of the American Chemical Society" 96: 4326 (1974)).

The nucleosides which are related to coformycin and which are separated according to the process of this invention include isocoformycin, 2'-deoxycoformycin and formycins. Isocoformycin has the formula:

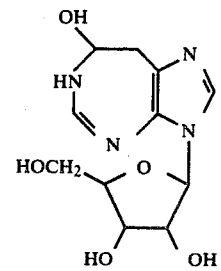

and is an unusual nucleoside which is chemically synthesized by the present inventors with co-inventors and which remarkably inhibits the enzymatic activity of adenosine deaminase (see Japanese patent application No. 110219/76 filed on Sept. 14, 1976). 2'-Deoxycoformycin is an unusual nucleoside discovered by certain American researchers and isolated from the culture broth of *Streptomyces antibioticus* and is an inhibitor against the enzymatic activity of adenosine deaminase (see the "Journal of Heterocyclic Chemistry" 11, 641 (1974)).

2'-Deoxycoformycin has the following formula:

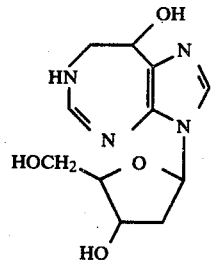

Hithertofore, the isolation and purification of coformycin from its related nucleosides usually required very troublesome operations either when coformycin was to be recovered from the culture broth of the Streptomyces strains, or when coformycin was to be recovered from the reaction mixture as formed in the chemical synthesis thereof. For instance, the culture broth of the coformycin-producing strains usually contains formycins A and B and other nucleosides in addition to the desired coformycin, and coformycin itself is very unstable under acidic conditions. Owing to these facts, it was normally required in the isolation and purification of coformycin to repeat chromatographic operations by adsorption and elution using a strong cation-exchange resin, activated carbon and a cation-exchanger such as a cross-linked dextran having basic function, for example, DEAE-Sephadex (a product of Pharmacia Co., Sweden) as described in Japanese patent publication No. 12278/70.

Accordingly, we have researched an attempt to devise an improved process for the isolation and purification of coformycin in order to recover coformycin in isolated and pure state from an aqueous solution of a crude powder comprising coformycin together with at least one of its related nucleosides. As a result, we have now found that coformycin can be isolated and purified in a facile way and in a high yield when a column chromatographic process is applied to said aqueous solution using a cation-exchanger having partially activated carboxylic groups as the ion-exchange function, and that coformycin can then be obtained easily in a pure crystalline form. It is to be noted that any cation-exchanger having carboxylic groups as the ion-exchange function has hithertofore never been employed for the chromatographic isolation and purification of coformycin from its related nucleosides. Furthermore, we have found that the chromatographic process using the cation-exchanger having partially activated carboxylic groups is generally applicable to said aqueous solution containing at least two of coformycin and its related nucleosides in order to separate them from each other.

DETAILED DESCRIPTION OF THE INVENTION

Accordingly, the generic aspect of this invention provides a process for separating coformycin from a mixture of coformycin with at least one of its related nucleosides, optionally with isolation of each component of the related nucleosides, which comprises subjecting a solution containing said mixture dissolved in water to column chromatography on a cation-exchanger having partially activated carboxylic groups as the ion-exchange function thereof and developing with water or a buffer solution, collecting in fractions the eluate flowing out of the column of the cation-exchanger in such a manner that the fractions each containing solely coformycin are collected optionally with collecting either the fractions each containing solely one of the related nucleosides or the other fractions each containing at least one of the related nucleosides, and then recovering coformycin from the fractions containing solely coformycin.

According to a first embodiment of this invention, there is provided a process in which separation of coformycin and its related nucleosides co-existing with the coformycin is achieved to isolate them from each other and which process comprises subjecting an aqueous solution of coformycin and at least one of its related nucleosides to column chromatography on a cation-exchanger having partially activated carboxylic groups as the ion-exchange function thereof and developing with water or a buffer solution, collecting in fractions the eluate flowing out of the column of the cation-exchanger in such a manner that there are collected separately the fractions each containing solely coformycin and the fractions each containing solely one of the other nucleosides, and then recovering separately coformycin and every one of the other nucleosides from the relative fractions containing solely the nucleoside to be recovered.

According to a second embodiment of this invention, there is provided a process in which separation of coformycin is achieved from a mixture of coformycin with at least one of its related nucleosides being the formycins, isocoformycin and 2'-deoxycoformycin and which process comprises subjecting an aqueous solution of said mixture to column chromatography on a cation-exchanger having partially activated carboxylic groups as the ion-exchange function thereof and developed with water or a buffer solution, collecting in fractions the eluate flowing out of the column of the cation-exchanger, in such a manner that the fractions containing solely coformycin are collected separately from the other fractions containing at least one of the formycins, isocoformycin and 2'-deoxycoformycin, and then recovering coformycin from the fractions containing solely coformycin.

In the process of this invention, it is necessary that the ion-exchange carboxylic groups of the cation-exchanger employed are partially activated, i.e. that the hydrogen ion ($H^+$) of each carboxylic group (—COOH) of the cation-exchanger has been replaced by the ammonium cation ($NH_4^+$) or an alkali metal cation such sodium, potassium and lithium so that the carboxylic group has been converted into an ammonium carboxylate group (hereinafter called $NH_4^+$-form) or an alkali metal carboxylate group (hereinafter called $Na^+$-form, $K^+$-form or $Li^+$-form). By partially activated carboxylic groups is meant a part of the total number of the carboxylic groups existing in said cation-exchanger has been activated by conversion into the carboxylate group. In the process of this invention, a cation-exchanger in which 50% to 70% of the total number of the carboxylic groups existing as the cation-exchange function has been activated is preferred for use, because such partially activated cation-exchanger exhibits superior performance to achieve the chromatographic isolation of coformycin.

For the cation-exchanger which is used in the process of this invention, a polyacrylic or polymethacrylic acid resin is most suitable. Cation-exchange resins consisting of a copolymer of methacrylic acid and divinylbenzene which are available commercially under a tradenames "Amberlite" CG-50, "Amberlite" IRC-50 and "Amberlite" IRC-84 (products of Rohm & Haas Co., U.S.A.) may be employed for the purpose of the invention. A cation-exchange resin consisting of a methacrylic acid resin which is available commercially under the tradename "Duolite" CC-3 (a product of Diamond Shamrock Chemical Co., U.S.A.), as well as cation-exchange resins which are available under the tradename "Lewatit" CNP (a product of Naftone Inc., U.S.A.) and under the tradename "Bio-Rex" 70 (a product of Bio-Rad Laboratories, U.S.A.) are suitable, too. It is preferred to use a cation-exchange resin having a small and uniform grain size, such as "Amberlite" CG-50, I-type (100–200 mesh) and II-type (200–400 mesh). It is preferred to use a cation-exchange polyacrylic resin in which the hydrogen-ion ($H^+$) of the carboxylic group of the resin is replaced by a mono-valent cation such as $NH_4^+$, $Na^+$, $K^+$ and $Li^+$ for the activation. The cation-exchange resin having partially activated carboxylic groups may be prepared in such a way that (i) a cation-exchange resin in which 100% of the carboxylic groups of this resin remains as the free carboxylic acid group (—COOH) (which may be called as a resin of 100% $H^+$-form) and (ii) a cation-exchange resin in which 100% of the carboxylic groups of this resin has been converted into the ammonium, sodium, potassium or lithium carboxylate groups (which may be called as a resin of 100% carboxylate-form, for example 100% $NH_4^+$-form, 100% $Na^+$-form, 100% $K^+$-form or 100% $Li^+$-form) are well admixed with each other in a volume of distilled water (preferably, one free from carbon dioxide dissolved therein) at a proper ratio of resin (ii) to resin (i), preferably at a ratio of 40 parts by volume or more of the resin of 100% $NH_4^+$-form (ii) to 60 parts by volume or less of the resin of 100% $H^+$-form (i), such that the total volume of the resins (i) and (ii) amounts to 100 parts. Alternatively, the cation-exchange resin having partially activated carboxylic groups may be prepared by equilibration with a buffer solution (preferably a phosphate buffer solution) having a pH of 6.6 or more and particularly a pH of 7.0–7.4. It is preferred to use such a cation-exchange resin having carboxylic groups partially activated to the extent that 50–70% of the whole carboxylic groups of the resin have been converted into carboxylate groups, or to the extent that the apparant pH of the resin is in a range of 7.0–7.4. Herein the apparent pH of the resin means the pH value of the water remaining externally adherded to the resin having partially activated carboxylic groups which has been prepared by well mixing a resin of 100% $H^+$-form with a resin of 100% carboxylate-form in a volume of distilled water and then collecting the resin by filtration. It is also feasible to use such a cation-exchange resin having partially activated carboxylic groups which has been prepared by mixing with a buffer solution of a pH of 7.0–7.4 until the buffer solution will show a pH value of 7.0–7.4 at equilibrium.

In carrying out the process of this invention, the partially activated cation-exchanger, that is, the cation-exchanger having partially activated carboxylic groups used according to this invention may be packed in a cylindrical column of which the ratio of the height to the diameter is 10:1 or more, and the aqueous solution containing coformycin and its related nucleoside(s) to be separated is placed on the top of the column of the cation-exchanger. The column chromatography is then effected using water as the developing solvent, so that separation and purification of coformycin and the related nucleoside(s) are achieved. It is preferred that the volume of the aqueous solution containing coformycin and its related nucleoside(s) to be separated which is placed on the top of the cation-exchanger column should be not more than one-fifth of the volume of resin bed. It is most preferred to use as the developing solvent for the column chromatography a distilled water which contains no carbon dioxide dissolved therein. It is also possible to employ a buffer solution containing an alkali metal phosphate such as sodium phosphate or potassium phosphate at a concentration of no more than 1/10 M as the developing solvent.

The process of this invention is very effective to effect the isolation and purification of coformycin when coformycin is recovered from the culture broth of the coformycin-producing microorganisms in which large amounts of formycins A and B co-produced are accumulated in addition to coformycin. Thus, a filtrate of the culture broth of the coformycin-producing strain which also produces formycins may be passed through a column of a strong cation-exchange resin for the adsorption of coformycin and formycin A. This cation-exchange resin column may then be eluted with a diluted aqueous solution of ammonia, the eluate collected in fractions, and the active fractions containing both of coformycin and formycin A combined and concentrated to dryness under reduced pressure to give a crude powder containing both coformycin and formycin A. This crude powder may be dissolved in a small volume of water and the resulting aqueous solution containing coformycin and formycin A may be chromatographed according to the process of this invention by passing through a column of a weak cation-exchanger, Amberlite CG-50 of 50–70% $NH_4^+$-form, followed by the development with water. In this chromatographic process, coformycin is eluted at first and formycin A is then eluted in an elution pattern separate from that of coformycin. The fractions containing solely coformycin are collected from the eluate, while the fractions containing solely formycin A are also collected. The coformycin-containing fractions are combined and concentrated to dryness under reduced pressure to give a powder of coformycin which is, in turn, crystallized from water to afford crystals of pure coformycin. The formycin-containing fractions may be processed in the same way as above to afford crystals of pure formycin A. Coformycin and formycin A which are present together can be separated from each other by the process of this invention, and also isocoformycin and 2'-deoxycoformycin which are present together can be separated from each other by the process of this invention. Accordingly, the process of this invention is utilisable to effect the isolation and purification of coformycin or isocoformycin when coformycin or isocoformycin is to be recovered from the reaction mixture formed in the chemical synthesis of coformycin or isocoformycin. When the process of this invention is applied to high-performance liquid chromatography with using an ultra-violet light detector, it is possible to make the separation and quantitative analysis of coformycin and its related nucleosides.

This invention is now illustrated by the following Examples to which this invention is in no way limited.

EXAMPLE 1

A weakly acidic cation-exchange resin having carboxylic groups as the ion-exchange functions and consisting of a copolymer of methacrylic acid and divinylbenzene (100% $H^+$-form, available as "Amberlite" CG-50, I-type, a commercial product of Rohm & Haas Co., U.S.A.) was treated with aqueous ammonia to convert all the carboxylic groups of resin into the ammonium carboxylate groups, so that the 100% $NH_4^+$-form was prepared. This cation-exchange resin of the 100% $NH_4^+$-form and the aforesaid cation-exchange resin of the 100% $H^+$-form in a ratio of 7:3, 1:1, 4.5:5.5, 4:6 and 3:7 by volume were placed in a volume of distilled water (free from carbon dioxide dissolved therein) and the admixture was agitated well. In this way, the cation-exchange resin of the 70% $NH_4^+$-form, the cation-exchange resin of the 50% $NH_4^+$-form, the cation-exchange resin of the 45% $NH_4^+$-form, the cation-exchange resin of the 40% $NH_4^+$-form and the cation-exchange resin of the 30% $NH_4^+$-form were prepared. A volume (10 ml) of the cation-exchange resin so prepared was packed into a glass tube of 9 mm internal diameter to form a resin column through which an aqueous solution containing 5 mg of coformycin and 5 mg of formycin A per 1.5 ml of water (pH 6.8) was then passed from the top of the resin column. The resin column was thereafter developed with water at a flow rate of 30 ml/hour. The effluent running out of the column was collected in 2 ml-fractions. Each fractions was analyzed by a thin-layer chromatography on silica gel developed with butanol-methanol-water (4:1:2 by volume): the presence of coformycin was detected at Rf 0.29 and the presence of formycin A at Rf 0.45 by ultraviolet light irradiation. The results of these tests are tabulated below. As will be clear from the results of the following table, coformycin can be satisfactorily separated from formycin A.

Table 1

| Cation-exchange resin $NH_4^+$-form | Apparent pH of resin | Eluate fraction Nos. containing coformycin | Eluate fraction Nos. containing formycin A |
|---|---|---|---|
| 100% | 8.6 | 4–6 | 5–7 |
| 70% | 7.4 | 7–10 | 10–14 |
| 50% | 7.0 | 13–18 | 18–24 |
| 45% | 6.8 | 16–26 | 19–28 |
| 40% | 6.6 | 19–30 | 21–35 |

Table 1-continued

| Cation-exchange resin | | | |
|---|---|---|---|
| $NH_4^+$-form | Apparent pH of resin | Eluate fraction Nos. containing coformycin | Eluate fraction Nos. containing formycin A |
| 30% | 6.2 | 33–52 | 33–52 |

Fraction Nos. 7–9 of the eluate obtained from the column of the 70% $NH_4^+$-form were combined and the combined solution was concentrated to dryness under reduced pressure, affording a colorless crystalline coformycin. mp. 182°–184° C. Yield. 4.8 mg. (96%). In the same manner as above, coformycin was recovered as a colorless crystalline product (mp. 182°–184° C.) from fraction Nos. 13–17 of the eluate obtained from the 50% $NH_4^+$-form. Yield 4.8 mg (96%).

Fraction Nos. 11–14 of the eluate obtained from the 70% $NH_4^+$-form were combined and the combined solution was concentrated to dryness under reduced pressure, affording a colorless crystalline product of formycin A. mp. 141°–142° C. Yield 4.5 mg (90%). In the same way as above, formycin A was recovered as a colorless crystalline product (mp. 141°–142° C.) from fraction Nos. 19–24 of the eluate obtained from the column of the 50% $NH_4^+$-form. Yield 4.6 mg (92%).

EXAMPLE 2

A solution containing 2.0 mg of coformycin and 1.8 mg of 2'-deoxycoformycin per 1 ml of water (pH 7.0) was passed through a column (5 mm diameter) of 5 ml of the cation-exchange resin, Amberlite CG-50 (I-type) 50% $NH_4^+$-form which was prepared in the same way as in Example 1. The resin column was developed with water (free from carbon dioxide dissolved therein) for the chromatography, and the eluate was collected in 1 ml-fractions. Each fraction was analyzed by silica gel thin-layer chromatography in the same manner as described in Example 1. It was found that coformycin was eluted only in fraction Nos. 14–20 separately from the fraction Nos. 21–29 in which 2'-deoxycoformycin (Rf 0.33 in the above-mentioned silica gel thin-layer chromatography) was eluted out. Fraction Nos. 14–20 were combined together and concentrated to dryness under reduced pressure to give a colorless crystalline product of coformycin. mp. 182°–184° C. Yield 100%. In a similar way, 2'-deoxycoformycin was recovered as a colorless crystalline product (mp. 220° C.) from fraction Nos. 21–29 of the eluate. Yield 100%.

EXAMPLE 3

A culture broth filtrate (2000 ml, pH 7.4, containing 26 mg of coformycin, 120 mg of formycin A and an unknown amount of formycin B) obtained from the submerged cultivation of a coformycin-producing microorganism, *Nocardia interforma* (ATCC No. 21072) was passed through a column (28 mm diameter) of 110 ml of a strong cation-exchange resin consisting of a polystyrene sulfonic acid (available as "Amberlite" IR-120, a commercial product of Rohm & Haas Co., U.S.A.) which had been converted into the 50% $NH_4^+$-form prepared as described in Example 1. Coformycin and formycin A in the culture filtrate were adsorbed on the resin, but formycin B was not adsorbed. The resin column was washed with 550 ml of water and then eluted with 1 N aqueous ammonia. The first running (70 ml) was discarded, and the eluate was recovered (250 ml) after its pH increased to 9.6 or more. The recovered eluate containing coformycin and formycin A was concentrated to dryness under reduced pressure to give 725 mg of a crude powder. This crude powder was dissolved in 4 ml of water and the resulting aqueous solution (pH 9.0) was subjected to a column chromatography with a column (15 mm diameter) of 40 ml of "Amberlite" CG-50 (I-type) of 50% the $NH_4^+$-form. The development was done with water. The eluate was collected in 4 ml-fractions. Each fraction was analysed by silica gel thin-layer chromatography in the same manner as described in Example 1. Fraction Nos. 28–34 containing coformycin alone were combined and concentrated to dryness under reduced pressure to give 43 mg of a colorless powder. This powder was crystallised from 0.6 ml of warm water, affording 19 mg of colorless crystals of coformycin. mp. 182°–184° C. Yield 73%. Fraction Nos. 35–61 containing formycin A alone were combined and concentrated to dryness under reduced pressure to give 135 mg of a colorless powder. This powder was crystallised from 4 ml of warm water, affording 90 mg of colorless crystals of formycin A. mp. 141°–142° C. Yield 75%.

EXAMPLE 4

A solution of 410 mg of 2',3',5'-tri-O-acetyl-6-mesyloxymethyl-1,6-dihydropurine riboside in 10 ml of 1,2-dimethoxyethane was admixed with 10 ml of 1 N aqueous sodium hydroxide, and the mixture was agitated for 16 hours at ambient temperature to effect the reaction for the synthesis of isocoformycin. The reaction solution was concentrated by distilling out the dimethoxyethane under reduced pressure. The residue so obtained was admixed with water to a volume of 50 ml, and the solution was adjusted to pH 7 by the addition of aqueous acetic acid. The aqueous solution so obtained was passed through a column of 80 ml of a strong cation-exchange resin, Dowex 50W×2 (100% $NH_4^+$-form, a commercial product of Dow Chemical Co., U.S.A. consisting of a copolymer of divinylbenzene and styrene sulfonic acid). This resin column containing the desired reaction product adsorbed therein was eluted with 0.5 N aqueous ammonia. The eluate was concentrated to dryness under reduced pressure to yield 175 mg of a yellow colored powder comprising coformycin and isocoformycin. This powder was dissolved in 0.5 ml of water and the aqueous solution obtained (pH 7.0) was passed through a column (6 mm diameter) of 15 ml of Amberlite CG-50 (I-type) of the 50% $NH_4^+$-form, which was then developed with water. The effluent was collected in 1.5 ml-fractions. Fraction Nos. 32–40 containing solely coformycin were combined and concentrated to dryness under reduced pressure, affording 12 mg of colorless crystals of coformycin. mp. 182°–184° C. Fraction Nos. 65–105 containing solely isocoformycin were combined and concentrated to dryness under reduced pressure, affording 53 mg of a colorless powder of isocoformycin. mp. 168°–172° C.

EXAMPLE 5

Aliquinots a weak cation-exchange resin, Amberlite CG-50 (II-type, 100% $Na^+$-form) were admixed with 0.02 M sodium phosphate buffer solutions of pH 7.0, pH 7.4 or pH 7.8 and the mixtures stirred at ambient temperature until the pH values of the buffer solutions reached an equilibrium. The cation-exchange resins so prepared were each packed into a stainless steel column having 2.2 mm internal diameter and 500 mm height. 5

μl of an aqueous solution of 500 μg/ml of coformycin, 5 μl of an aqueous solution of 500 μg/ml of formycin A or 5 μl of an aqueous solution of 500 μg/ml of isocoformycin was injected into the top of the resin column by means of a micro-syringe, and high performance liquid chromatography was conducted at ambient temperature using 0.02 M sodium phosphate buffer solution of pH 7.0, pH 7.4 or pH 7.8 as the developing solvent. The developing solvent was passed at a flow rate of 60 ml/hour. The presence of the nucleosides was detected by the ultra-violet light detector at 280 nm.

A varian Aerograph LC-4200 System (obtained from Varian Instruments, U.S.A.) was used for the high-performance liquid chromatography. Retention time, i.e., the time lapsed between the injection of the sample solution and the appearance of the peak of the spectrophotometer readings of the ultra violet absorption of the eluate fractions, was measured.

The results are summarised in the following table.

Table 2

| pH of the buffer solution used for treatment of the resin (Estimated percentages of the number of the sodium carboxylate groups of the resin equilibrated by the buffer solution) | Retention time (min.) | | |
|---|---|---|---|
| | Coformycin | Formycin A | Isocoformycin |
| 7.0 (Ca. 60%-$Na^+$) | 1.8 | 3.4 | 2.4 |
| 7.4 (Ca. 65%-$Na^+$) | 1.6 | 3.0 | 2.0 |
| 7.8 (Ca. 70%-$Na^+$) | 1.4 | 2.2 | not tested |

As shown by the above table, coformycin, formycin A and isocoformycin were separable form each other. The content of the nucleoside in each fraction of the eluate was calculated from the height of the ultra-violet absorption peak of the fractions measured by the spectrophotometer.

What we claim is:

1. A process of separating coformycin from a mixture of coformycin with at least one related nucleoside selected from the group consisting of formycin A, formycin B, isocoformycin and 2' deoxycoformycin, optionally with isolation of each components of the related nucleosides, which comprises subjecting an aqueous solution containing said mixture to column chromatography on a cation-exchanger having carboxylic groups partially activated by conversion into ammonium carboxylic groups or alkali metal carboxylate groups as the ion-exchange function thereof and developing with water or a buffer solution having a pH of at least 6.6, collecting in fractions the eluate flowing out of the column in such a manner that the fractions each containing solely coformycin are collected, optionally collecting the fractions each containing solely one of the related nucleosides or the other fractions each containing at least one of the related nucleosides, and recovering coformycin from the fractions containing solely coformycin.

2. A process according to claim 1, which comprises subjecting a aqueous solution of coformycin and at least one of the related nucleosides to said column chromatography, collecting in fractions the eluate flowing out of the column in such a manner that there are collected separately the fractions each containing solely coformycin and the fractions each containing solely one of the related nucleosides, and then recovering separately coformycin and every one of the related nucleosides from the relative fractions containing solely the nucleoside to be recovered.

3. A process according to claim 1, which comprises subjecting an aqueous solution of a mixture of coformycin with at least one of the formycins, isocoformycin and 2'-deoxycoformycin to said column chromatography, collecting in fractions the eluate flowing out of the column in such a manner that the fractions each containing solely coformycin are collected separately from the other fractions each containing at last one of the formycins, isocoformycin and 2'-deoxycoformycin, and then recovering coformycin from the fractions containing solely coformycin.

4. A process according to claim 1, 2 or 3 in which there is employed a cation-exchanger in which 50–70% of the total number of the carboxylic groups present as the ion-exchange function has been activated by conversion into ammonium carboxylate groups or an alkali metal carboxylate groups.

5. A process according to claim 1, 2 or 3 in which the cation-exchanger comprises a polyacrylic acid resin or a polymethacrylic acid resin.

6. A process accordingly to claim 5 in which the cation-exchanger is one in which 50–70% of the total number of the carboxylic groups of the resin has been activated.

7. A process according to claim 1, 2 or 3 in which the cation-exchanger is one having partially activated carboxylic groups which has been prepared by mixing with a buffer solution of pH 7.0–7.4 until the buffer solution shows a pH value of 7.0–7.4 at equilibrium.

8. A process according to claim 1, 2 or 3 in which the development is effected with water.

9. A process according to claim 1, 2 or 3 in which the development is effected with a phosphate buffer solution.

* * * * *